United States Patent [19]

Rhodes

[11] 3,972,827

[45] Aug. 3, 1976

[54] SILVER DETECTING FORMULATION

[76] Inventor: William A. Rhodes, 4421 N. 13th Place, Phoenix, Ariz. 85014

[22] Filed: Sept. 12, 1975

[21] Appl. No.: 612,635

[52] U.S. Cl............................ 252/408; 23/230 R
[51] Int. Cl.$^2$........................................ G01N 31/22
[58] Field of Search.................. 23/230 R; 252/408

[56] References Cited
OTHER PUBLICATIONS

Skoog et al., "Fundamentals of Analytical Chemistry," Holt, Rinehart and Winston, Inc., 1963, p. 111.

Bullock, "Simplicity of Mechanism of Reaction as one of the Factors Conditioning Catalysis," J. Phys. Chem. vol. 28, 1924, pp. 179 – 181.

Epik et al., "Relation of the Stability of Some Oxygen–Containing Inorganic Compounds to the pH of the Medium," Chem. Abstr., vol. 53, 1959, No. 21333d.

Milyutin et al., "Oxidation of Copper in Aqueous Solutions of Potassium Dichromate–Sulfuric Acid," Chem. Abstr. vol. 51, 1957, No. 12618i.

Taskarin, "Photometric Methods for Silver Determination," Chem. Abstr., vol. 71, 1969, No. 27224d.

Yatsimirskii et al., "Thermochemical Investigation of Solutions of Chromium Anhydride in Sulfuric Acid," Chem. Abstr. vol. 51, 1957, No. 3265d.

*Primary Examiner*—Morris O. Wolk
*Assistant Examiner*—Arnold Turk

[57] ABSTRACT

A chemical silver detecting formulation comprising approximately 300 ml. of water; approximately 36 grams of sulfuric acid having a specific gravity of approximately 1.275; and approximately 24 grams of potassium-dichromate. Additionally, the solution includes a copper sulphate ranging between 30 grams and 40 grams.

2 Claims, No Drawings

SILVER DETECTING FORMULATION

BACKGROUND OF THE INVENTION

It has been a problem to detect the purity of silver in a short period of time and it has usually been necessary to apply silver detecting solutions to bar silver or other large pieces of silver and rub the material on the silver for a considerable period of time or to wait for a considerable period of time for the desired indications to transpire. Usually the silver detecting formulations of the prior art have been used to induce certain colors to appear on the surface of the metal so as to determine the relative purity of the metal and thereby detect the relative value of a given piece of silver.

The prior art has heretofore required considerable inconvenience and time consuming effort and this has been an inconvenience to the necessity to rapidly detect the relative purity of the piece of silver.

Various prior art chemical formulas for the detection of silver have been extremely limited because they tend to show various colors among other metals which are confusing especially when silver happens to be mixed with them or alloyed with them.

SUMMARY OF THE INVENTION

The present invention comprises a combination of the foregoing chemicals which in a solution and when applied to silver of fine purity produces a vermillian color and this color occurs when the silver has a 99.9 percent purity and the solution of the invention produces a dark red to reddish brown for silver of sterling quality which is approximately 92.5 percent pure silver and also for U.S. coin silver containing approximately 90 percent silver. The solution of the invention when applied to all other heavy metals which appear to be silver, in other words white metals, the solution shows no color at all and therefore quickly discriminates between silver and other white metals. The use of sulfuric acid in the formulation relates to silver and is particularly important since other acids such as nitric acid may tend to indicate varying degrees of other colors relative to other metals which would be very confusing in the testing of an alloy having silver and other metals therein. Accordingly, the use of sulfuric acid in the formulation relative to the other materials is of substantial importance for discriminatory color production relative to silver only.

The use of copper sulphate in the solution or formulation provides immediate color rendition of a vermillian hue for the fine silver having approximately 99.9 percent purity. The use of the copper sulphate also provides rapid color rendition in the dark blood color on silver having a purity ranging between 90 and 92.5 percent and silver of lesser purity below 90 percent causes the color to rapidly turn to a muddy black which may be a reaction comparable to the indication of sterling silver.

Accordingly, it is an object of the invention to provide a chemical silver detecting formulation which when applied to a bar of silver will very quickly determine by coloration silver of a relative purity from 99.9 percent to a silver having a relative purity below 90 percent with excellent color contrast.

Another object of the invention is to provide a chemical silver detecting formulation which is capable of very rapidly and quickly detecting the relative purity of silver with a minimum of effort and time.

Another object of the invention is to provide a chemical silver detecting formulation which may be used on all white metals and which does not react to those which are alloys of materials other than silver.

Other objects and advantages of the invention may be apparent from the following specification and appended claims.

DESCRIPTION OF THE PREFERRED EMBODIMENTS

The chemical silver detecting formulation of my invention has for example; comprises the following elements in substantially the following portions: 300 ml. of water; approximately 36 grams of sulfuric acid having a specific gravity of approximately 1.275 which is battery acid quality and approximately 24 grams of Potassium-Dichromate. Additionally the solution includes copper sulphate ranging between 30 grams and 40 grams. While the foregoing figures represent the relationship of the elements, it will apparent to those skilled in the art that larger amounts of all of the foregoing elements may be put together in the same proportional relationship.

There are numerous chemical formulas on the market and in the literature for detection of silver but these are all limited because they tend to show various colors among other metals which are confusing especially when silver happens to be mixed with them.

My invention comprises a combination which produces a strong vermillian color for 99.9 percent fine silver and a dark red to red/brown for sterling containing 92.5 percent silver and U.S. coin silver containing 90 percent silver. One of the main purposes and objects of this formula is that it tends to show no color at all for all other heavy metals which look like silver. Thus my invention becomes a specific indicator for silver.

When water, sulfuric acid and Potassium-Dichromate are mixed and dissolved near the proportions shown, such a solution shows this property. Potassium-Dichromate will accomplish the same thing with another acid such as nitric however the presence of other acids causes other metals to show varying degrees of other colors and becomes very confusing when the user is trying to quickly determine silver alone.

The result I obtain with my formula is optimum using the following proportions: 300 ml. water, 36 grams sulfuric acid of specific gravity of 1.275 (battery acid quality) and 24 grams Potassium-Dichromate.

When totally dissolved, this formula works as described, however, it is slow and the user has to apply the solution several times on clean metal to obtain the optimum brilliant vermillion color on 99.9 percent fine silver.

I have improved on this formula by addition of 30 to 40 grams Copper sulphate. This changes the orange color of the solution to a straw color and it also provides immediate color rendition of the vermillion for 99.9 percent fine silver, to the color of dark blood on 90 to 92.5 percent fineness. Below 90 percent fine the color rapidly turns brown and with even less silver eventually a muddy black.

As copper-sulfate is reduced to where the straw color of the solution retains some of the dichromate orange coloration, speed of visual testing is reduced considerably.

The quantities of sulfuric acid and water were chosen so as to put the amount of dichromate shown into solution; it being noted that any lesser amounts of all components shown (except water) causes a slow-down of reaction time from instentaneous; while more than those amounts are a waste of chemicals because such does not increase the speed of the test color reaction. Of course an increase of water naturally causes dilution and again a slowing of test reaction time.

This formula will show no color at all on other metals resembling silver including, tin, lead, antimony, type metal, zinc etc., or combinations of them. In fact the tests were extended to most white metals with the same result.

It will be obvious to those skilled in the art that various modifications may be resorted to without departing from the spirit of the invention.

I claim:

1. A silver detecting formulation comprising the following elements in substantially the following proportions: approximately 300 ml. of water; approximately 36 grams of sulfuric acid, having a specific gravity of approximately 1.275; and approximately 24 grams of potassium-dichromate.

2. The invention as defined in claim 1, wherein: said solution also contains copper sulfate ranging between 30 grams and 40 grams.